US008774487B2

(12) United States Patent  (10) Patent No.: US 8,774,487 B2
Levine et al.  (45) Date of Patent: Jul. 8, 2014

(54) METHOD AND APPARATUS FOR REMOTELY PERFORMING HEMATOLOGIC ANALYSIS UTILIZING A TRANSMITTED IMAGE OF A CENTRIFUGED ANALYSIS TUBE

(76) Inventors: Joshua D. Levine, Chapel Hill, NC (US); Robert A. Levine, Guilford, CT (US); Stephen C. Wardlaw, Lyme, CT (US); Craig Stout, Port Matilda, PA (US); David A. Clipper, State College, PA (US)

( * ) Notice: Subject to any disclaimer, the term of this patent is extended or adjusted under 35 U.S.C. 154(b) by 434 days.

(21) Appl. No.: 13/016,392

(22) Filed: Jan. 28, 2011

(65) Prior Publication Data

US 2011/0200239 A1  Aug. 18, 2011

Related U.S. Application Data

(60) Provisional application No. 61/305,449, filed on Feb. 17, 2010, provisional application No. 61/351,138, filed on Jun. 3, 2010.

(51) Int. Cl.
G06K 9/00  (2006.01)

(52) U.S. Cl.
USPC .......................................................... 382/134

(58) Field of Classification Search
CPC .................................................. B01L 3/50215
USPC ........................................ 382/133, 134, 128
See application file for complete search history.

(56) References Cited

U.S. PATENT DOCUMENTS

| 4,027,660 | A |   | 6/1977  | Wardlaw et al.          |
|-----------|---|---|---------|-------------------------|
| 4,091,659 | A |   | 5/1978  | Massey, III et al.      |
| 4,137,755 | A |   | 2/1979  | Wardlaw et al.          |
| 4,209,226 | A |   | 6/1980  | Wardlaw et al.          |
| 4,404,683 | A | * | 9/1983  | Kobayashi et al. ... 382/134 |
| 4,558,947 | A |   | 12/1985 | Wardlaw                 |
| 4,683,579 | A |   | 7/1987  | Wardlaw                 |
| 5,132,087 | A |   | 7/1992  | Manion et al.           |
| 5,888,184 | A |   | 3/1999  | Wardlaw                 |
| 6,197,523 | B1|   | 3/2001  | Rimm et al.             |

(Continued)

OTHER PUBLICATIONS

Marcus, Uniform Laser Scanning in a Hematology Analyzer [online], Jun. 2002 [retrieved Feb. 18, 2014], IEEE Instrumentation & Measurement Magazine, vol. 5, Issue: 2, pp. 24-27. Retrieved from the Internet: http://ieeexplore.ieee.org/xpls/abs_all.jsp?arnumber=1005656&tag=1.*

(Continued)

*Primary Examiner* — Matthew Bella
*Assistant Examiner* — Dennis Rosario
(74) *Attorney, Agent, or Firm* — O'Shea Getz P.C.

(57) ABSTRACT

An apparatus for and method of analyzing hematologic samples deposited within a capillary tube is provided. The method includes the steps of: a) imaging a region of sample centrifuged within a capillary tube using a first analysis device, which region is defined by substantially all of the radial width and axial length of the sample residing within the internal cavity of the tube where the float resides after centrifugation, and producing signals representative of the image; b) communicating the signals representative of the image to a second analysis device independent of, and remotely located from, the first analysis device; c) processing the signals representative of the image using the second analysis device and producing analysis data based on the signals; and d) displaying the image of the region of the sample using the second analysis device.

20 Claims, 1 Drawing Sheet

(56) References Cited

U.S. PATENT DOCUMENTS

| | | |
|---|---|---|
| 6,441,890 B2 | 8/2002 | Wardlaw |
| 6,506,606 B1 | 1/2003 | Winkelman et al. |
| 6,911,315 B2 * | 6/2005 | Rimm et al. .................. 435/7.22 |
| 7,129,056 B2 * | 10/2006 | Rimm et al. .................. 435/7.24 |
| 7,982,201 B2 * | 7/2011 | Bryant et al. .................. 250/577 |
| 2008/0179301 A1 | 7/2008 | Garty et al. |

OTHER PUBLICATIONS

"Star Tube User Guide", QBC Star, Centrifugal Hematology System, QBC Diagnostics Inc., www.qbcdiagnostics.com.

Zaitsev et al. "A Device for Automated Detection and Analysis of the Erythrocyte Sedimentation", vol. 43, No. 3, 2009, pp. 131-134.

International Search Report dated Mar. 26, 2011.

* cited by examiner

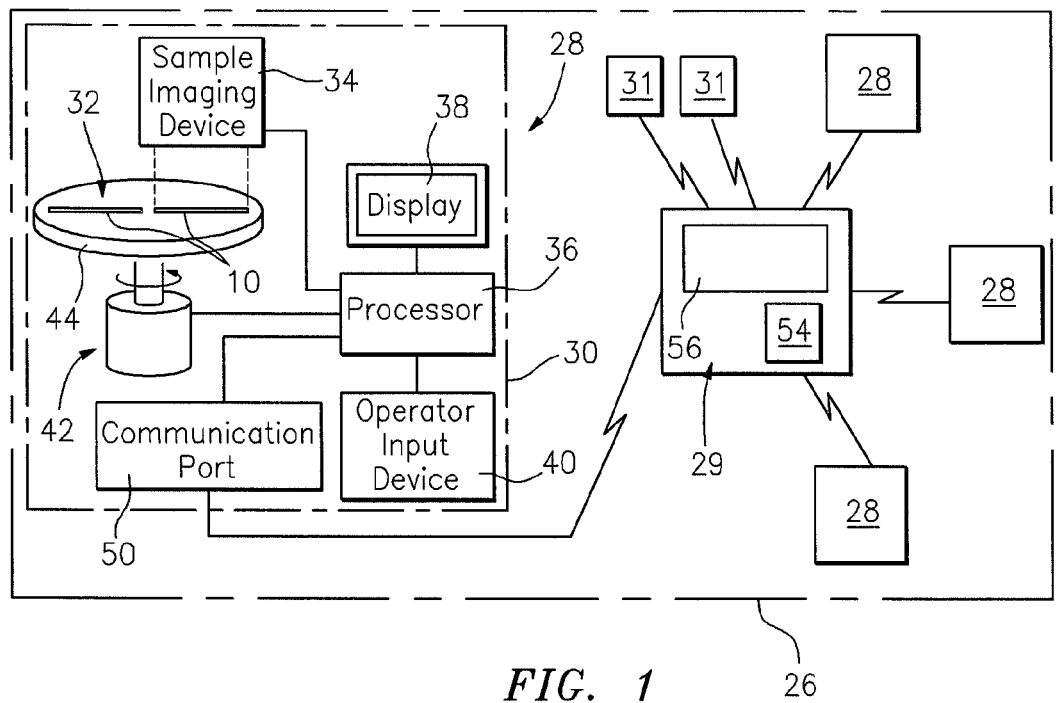
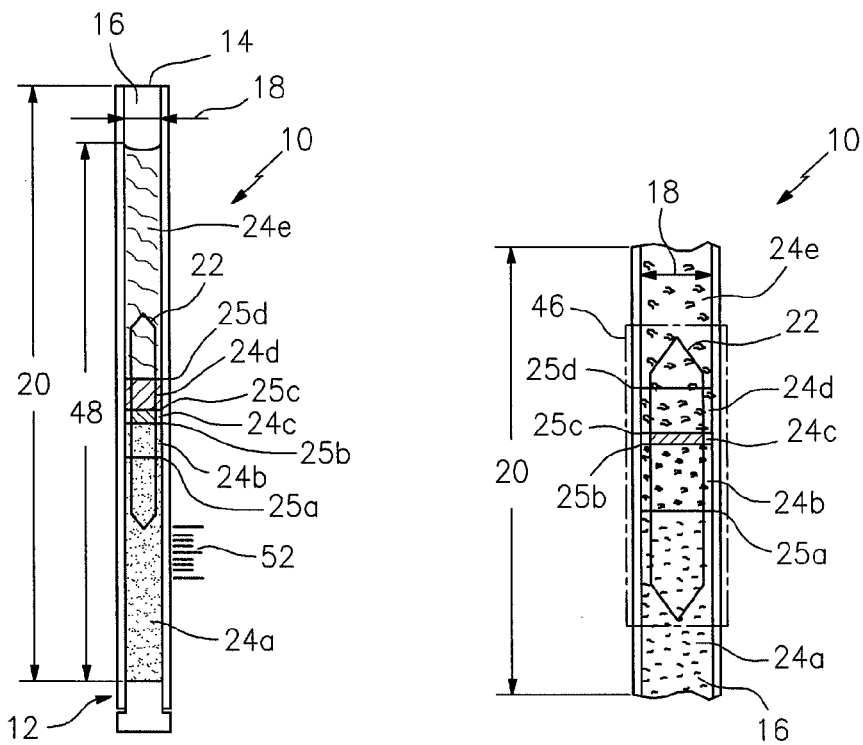
FIG. 1
FIG. 2 (PRIOR ART)
FIG. 3 (PRIOR ART)

METHOD AND APPARATUS FOR REMOTELY PERFORMING HEMATOLOGIC ANALYSIS UTILIZING A TRANSMITTED IMAGE OF A CENTRIFUGED ANALYSIS TUBE

This application claims the benefit of U.S. Provisional Patent Application No. 61/305,449 filed Feb. 17, 2010 and U.S. Provisional Patent Application No. 61/351,138 filed Jun. 3, 2010, each of which applications is hereby incorporated by reference in its entirety.

BACKGROUND INFORMATION

U.S. Pat. Nos. 4,027,660; 4,091,659; 4,137,755; 4,209,226; 4,558,947; 4,683,579; 5,132,087; 5,888,184; and 6,441,890 describe methods and apparatus for hematological analysis using a capillary tube and a space occupying insert that floats on the centrifuged red blood cells thereby expanding the surrounding buffy coat and permitting the measurement and quantization of the blood's layers. This method permits the determination of a compete blood count (CBC) consisting of hematocrit, a hemoglobin determination, a total white blood cell count with the latter presented as a total and percent granulocytes and total and percent lymphocytes plus monocytes, as well as a platelet count and a mean red cell hemoglobin concentration. It is widely used through the world for performing point of care CBC in human and veterinary medicine. The device, formerly manufactured and sold by Becton Dickinson, Inc. of New Jersey U.S.A. is now manufactured and sold by QBC Diagnostics, Inc., of Pennsylvania, U.S.A. The apparatus is sold under the trademark of QBC® hematology. The capillary tubes are referred to in the industry as "QBC® tubes".

The QBC® hematology system includes a number of different complex instruments for reading the QBC® tubes, each of which has an illumination system, a power source, an imaging and optical system, a microprocessor, and a display. These devices can cost anywhere from several hundred to many thousands of U.S. dollars. The current versions of both the stand-alone reader and the integral reader-centrifuge (QBC® STAR reader) provide for a linear scan of the tube, either while it is stationary in the case of the stand-alone reader or while the centrifuge is in motion, as is the case with the QBC® STAR reader. In both cases, the linear scan is limited to scanning a single axially extending line scan of the tube, which evaluates only a thin stripe of the area of interest within the tube. Because this method of scanning can only scan a thin stripe of the area of interest at a given time, it is necessary to take multiple axially extending scans taken at different circumferential positions of the tube to determine which of the scans can be used for analytical purposes. By looking at several different scans, each taken at a different circumferential position, it is possible to ascertain whether any particular scan is representative of the sample or if it contains an unrepresentative anomaly. Also, because of the narrow scan, the mechanical and optical alignment of the instrument must be held to a very high tolerance, which also increases the cost of the device.

This is particularly true in the case of the QBC® STAR reader, because the QBC® tube is read while the centrifuge is in motion, necessitating an elaborate timing system to ensure that illumination occurs exactly when the tube is in position under the linear scanning device (e.g., CCD scanner). Another, related problem is the need to provide elaborate vibration damping so that the relative tube and reader position be maintained during this process.

These considerations cause the analysis tube readers to have a relatively high price, which limits the market size for the QBC® hematology system because health care providers are reluctant and/or unable to make the requisite equipment investment when the equipment is only used for a few tests per day. In those instances when the point of care giver does not have the analysis equipment, the patient is subjected to the significant inconvenience, harm and expense of having to go to a private laboratory and having to wait often several days to get the result. The lack of an analysis device also makes the physician's job more difficult by precluding immediate results at the point of care. Additionally, regulatory requirements of the United States require that the providers of the test be subject to regulatory supervision under the CLIA (Clinical Laboratory Improvement Act) laws.

What is needed, therefore, is a simple, inexpensive, robust method for reading the centrifuged blood sample at the point of care with immediate availability of results while the health care providers are still with the patient. In addition, a method and device are needed that can provide accuracy results and methodological adherence to proper analytic techniques, as well as quality control measures, particularly those that will permit CLIA waiving, which is subject to less burdensome regulations.

SUMMARY OF THE INVENTION

According to one aspect of the present invention, a system for analyzing a hematologic sample centrifuged within a capillary tube is provided. The tube has an internal compartment with a radial width and an axial length and a float disposed within the tube. The system includes at least one first analysis device and a second analysis device. The first analysis device includes a tube holder and a sample imaging device. The sample imaging device is adapted to create a digital image of the sample within a region of the tube. The region is defined by substantially all of the radial width and axial length of the sample residing within the internal cavity of the tube where the float resides after centrifugation. The sample imaging device is adapted to produce signals representative of the image. The second analysis device is adapted to be remotely located from the first analysis device, and to communicate with the first analysis device, including receiving the signals representative of the image. The second analysis device includes a processor and a sample data display. The processor is adapted to produce information relating to bands of interest within the image based on the signals. The sample data display is adapted to display the digital image of the sample within the region.

According to another aspect of the present invention, a method of analyzing hematologic samples deposited within a capillary tube is provided. The method includes the steps of: a) imaging a region of sample centrifuged within a capillary tube using a first analysis device, which region is defined by substantially all of the radial width and axial length of the sample residing within the internal cavity of the tube where the float resides after centrifugation, and producing signals representative of the image; b) communicating the signals representative of the image to a second analysis device independent of and remotely located from, the first analysis device; c) processing the signals representative of the image using the second analysis device and producing analysis data based on the signals; and d) displaying the image of the region of the sample using the second analysis device.

A significant advantage associated with the present analysis system is that it provides application versatility. For example, the present analysis system allows sample testing that requires trained personnel to be performed in health care offices without trained personnel. The sample can be centrifuged and imaged in the healthcare office, and the image sent to a remotely located analysis provider office where a trained technician can perform the analysis. In this manner, a single analysis provider office can service a significant number of healthcare offices. As a result, the level and speed of care available to the patient from the healthcare provider is increased. In fact, the ability of the present analysis system to bi-directionally communicate one or both of the image and the analysis results means that the testing can be performed in a very short period of time; e.g., seconds to minutes. The present analysis system also avoids the cost of providing a trained technician at each of the healthcare offices. Another advantage of the present analysis system is its quality control capability. As will be described hereinafter, the present system makes it possible to periodically (or randomly) check the accuracy of a local analysis device though a centrally located analysis device, which central device may be operated by a trained technician. In addition, the quality control analyses can include review functions such as a determination of whether an automated analysis algorithm applied to the centrifuged sample has properly placed the lines at the required interfaces (such as bottom of tube, bottom of float, red cell/granulocyte interphase, granulocyte/lymphocyte+monocyte interphase, lymphocyte+monocyte/platelet interphase, platelet/plasma interphase, top of float, plasma/air interphase, etc.), or a determination of whether sample has leaked from a tube during centrifugation, or whether the sample image includes an anomaly, etc.

The present analysis devices also provide advantage because they image the sample in a manner that eliminates many problems associated with narrow linear array sensing. The present analysis devices image substantially all of the radial width and a significant portion of the axial length of a centrifuged sample within a capillary tube. The narrow linear array sensing of the prior art, in contrast, is susceptible to circumferentially located bandwidth anomalies; e.g., if the bandwidth at a particular circumferential position is irregularly too small or too big, data based on that band width will be inaccurate. For this reason, the prior art devices take multiple linear array sensings at non-contiguous circumferential positions and average those sensings, or otherwise compare them to one another for accuracy. The prior art devices, therefore, require hardware that can rotate one or both of the linear sensing array and the sample. The hardware must also be able to provide very accurate mechanical and optical alignment of the instrument relative to the sample, and in the case of a dynamic sensing device like the QBC® STAR reader, also provide elaborate imaging controls and vibration damping.

On the other hand, the prior art linear imaging had the advantage of minimal geometric distortion. Since all prior art imaging data was in the form of a narrow linear segment taken at a right angle to the tube as it was scanned, each band position was exactly related to its digital representation. In the case of the image array as used in the present device, in which the tube is positioned some distance from the imaging lens and camera, the bands in the tube are foreshortened in proportion to their distance from the center of the optical axis, and the sides of the tube are particularly affected by this effect, sometimes making them appear crescent shaped. This geometric distortion, in addition to any other distortions from the lens, is preferably accounted for in order to enhance the accuracy of the results. For example, the geometric distortion can be accounted for by using a correction table which accounts for each pixel, or regions in the image. The correction table can be used to re-map the image so that the image positions correctly correspond to the actual locations on the tube surface. This type of correction table can be automatically generated by imaging and analyzing a known "calibration" standard or if only geometric distortion is involved, the corrections can be simply calculated based on the known distances involved. Alternatively, the geometric distortion can be accounted for by correcting the band lengths following their preliminary measurement.

The foregoing and other objects, features and advantages of the present invention will become more apparent in light of the following drawings and detailed description of the present invention.

BRIEF DESCRIPTION OF THE DRAWINGS

FIG. 1 is a schematic diagram of the present invention hematology analysis system.

FIG. 2 is a schematic diagram of a capillary tube.

FIG. 3 is an enlarged partial view of a tube such as that shown in FIG. 2.

DETAILED DESCRIPTION OF THE INVENTION

Referring to FIGS. 1 and 2, a blood sample for analysis within the QBC® hematology system is typically obtained either from a venous or capillary sample, centrifuged in a simple, small dedicated centrifuge which may be either battery powered or AC powered. U.S. Pat. Nos. 4,027,660; 4,683,579; 5,132,087 and 6,441,890, each of which is hereby incorporated by reference in its entirety, describe methods and apparatus for hematological analysis using a capillary tube and a space occupying insert that floats on the centrifuged red blood cells thereby expanding the surrounding buffy coat and permitting the measurement and quantization of the blood's layers. The capillary tube 10 includes a body that extends between a closed bottom 12 and an open top 14. In some embodiments, the "closed bottom" may be vented to allow the escape of gas. The open top 14 provides access to an internal cavity 16 that has a radial width 18 and an axially extending length 20. In those embodiments where the tube 10 is cylindrical, the radial width 18 is the inner diameter of the tube 10. The present invention is not limited to use with any particular type of capillary tube. U.S. Pat. No. 4,027,660, for example, describes a QBC® style capillary tube operable to contain a fluid sample and a volume occupying mass 22 (hereinafter referred to as a "float"), and the information available by virtue of the relative positioning of the float 22 within the sample after centrifugation. U.S. Pat. No. 6,444,436 describes a different style of capillary tube that can be used with the present invention; e.g., one having a polynomial (e.g., rectilinear) cross-sectional geometry. FIGS. 2 and 3 of the present application diagrammatically illustrates a capillary tube 10 with a sample and a float 22 disposed in the internal cavity 16 of the tube 10. The centrifuged sample disposed in the tube 10 illustrates the constituent bands 24 (24a, 24b, 24c, 24d, 24e) and the band boundaries 25 (25a, 25b, 25c, 25d) therebetween. U.S. Pat. Nos. 4,683,579 and 6,441,890 describe automated devices for reading the centrifuged sample by way of an axially extending linear scan of a limited portion of the sample disposed within the QBC® tube, which limited linear portion is disposed at a particular circumferential position of the tube 10.

Referring to FIG. 3, the present analysis system 26 includes one or more analysis devices 28 in communication with at least one remotely located analysis station 29. As will be described below, the analysis device 28 is in electronic communication with the at least one remotely located analysis station 29, which communication may be accomplished by hardwire connection or by wireless signal.

The analysis device 28 operates with a capillary tube 10 such as those provided within a QBC® hematology system; i.e., a tube 10 filled with a sample that has been centrifuged to produce the separated constituent layers 24 (also referred to as "bands"; see FIGS. 1 and 2) within the sample. One embodiment of the present analysis device 28 includes a housing 30 containing a tube holder 32, a sample imaging device 34, a processor 36 adapted to produce information relating to bands 24 of interest within the image based on the signals from the sample imaging device 34, and may include a sample data display 38 and an operator input device 40 that enables the operator to enter relevant patient information.

In some embodiments, the analysis device 28 further includes a centrifuge 42 with a platen 44 configured to hold one or more capillary tubes 10 in a position where the tubes 10 extend radially outward from a central axis. In these embodiments, the analysis device 28 can perform both the centrifugation and the image analysis. The centrifuge 42 is operable to centrifugally spin the tube 10 containing the sample about the central axis at speeds sufficient to create constituent layer separation within the sample disposed in the tube 10. In these embodiments, the platen 44 is an example of a tube holder 32. In other embodiments, the tube holder 32 may be independent of the centrifuge 42.

The sample imaging device 34 includes a digital camera operable to image substantially all of the radial width 18 and axial length 20 of the sample residing within the internal cavity 16 of the tube 10 in the region 46 (see FIG. 3) where the float 22 resides after centrifugation in a single image, and to produce signals representative of the image. In the preferred embodiments, the sample imaging device 34 is operable to image a region 48 comprising substantially all of the radial width 18 and axial length 20 of the sample within the tube 10 in a single image, and to produce signals representative of the image. Alternately, two or more cameras can be used to image separate portions of the tube 10, which portions are contiguous with one another. The images of the contiguous regions can be subsequently combined and analyzed or are separately analyzed. Either the digital camera itself, or an independent light source within the sample imaging device 34, provides sufficient lighting so that bands 24 of interest within the centrifuged sample may be differentiated within the sample image. The optical resolution of the camera used must be sufficient to provide adequate clarity within the image for the analysis at hand; e.g., to differentiate bands 24 of interest. As indicated above, the sample imaging device 34 may be incorporated into a QBC® tube type reader, or may be an independent device (e.g., a portable digital camera, a cell phone camera, etc.) configured for use with such a reader. An example of an acceptable digital camera is a Bayer-type matrix color camera. If, for example, a standard Aptina® five megapixel color camera chip with a frame width of 2592 pixels is used, it can produce a theoretical image resolution of 0.02 mm, which is acceptable for most analyses. If a color camera is used, color filters and different illumination types are likely not required. A grey scaled camera may also be used because the separated buffy coat layers have different light scattering properties and may therefore be detected using a black and white camera, although this measurement is less robust and requires more controlled illumination. The sample imaging device 34 may be described as an "area-array imaging device" because it images substantially all of the radial width 18 and axial length 20 of the sample within the interior cavity 16. If a plurality of cameras is used within the present sample imaging device 34, the images they produce are contiguous with one another thereby permitting the plurality of images to be combined into a single representative image. The linear scan devices of the prior art, in contrast, are limited to producing narrow circumferentially located linear segments that do not extend across the full radial width 18, which linear segments are not contiguous with each other. As a result, the circumferentially positioned linear segments cannot be combined into a single representative image Examples of acceptable independent light sources include white and/or blue LEDs, operable either in a steady state mode or in the case of the QBC® STAR type reader, in a pulsed mode. The relative blue spectrum of a white LED or the inclusion of a separate blue LED can excite the fluorescence of a dye such as Acridine Orange in the tube 10.

The processor 36 is adapted (e.g., programmed) to perform several tasks, including: a) controlling the sample imaging device 34 based on the analysis at hand; b) controlling the centrifuge 42 for those embodiments that include one; c) receiving and acting on operator input entered through the operator input device 40; in some embodiments d) producing information relating to bands 24 of interest within the image; and e) sending one or both of the signals from the sample imaging device 34 and the information relating to bands 24 of interest to one or more remotely located sample analysis stations 29. The extent of the information relating to the bands 24 produced by the processor 36 can be varied to suit the tasks at hand. For example, the processor 36 may be adapted to provide information relating to the adequacy of the sample image, and/or may be adapted with algorithmic capability for analyzing the signals representative of the sample image, and adapted to produce data (e.g., CBC, hematocrit, WBC count, etc.) relating thereto based on characteristics of the different bands 24 within the centrifuged sample. In some applications, the processor 36 can be adapted to produce graphic markings based on the analysis of the sample that can be superimposed over the sample image when displayed to illustrate the calculated band boundaries 25 relative to the sample image. Using blood analysis as an example, graphic markings can be used to identify features such as the: a) bottom of the tube 10; b) bottom of the float 22; c) red blood cell/granulocyte interphase; d) granulocyte/lymphocyte and monocyte interphase; e) lymphocyte and monocyte/platelet interphase; f) platelet/plasma interphase; g) top of the float 22; h) plasma/air interphase; etc.

For those analysis device 28 embodiments that include one, the sample data display 38 is in communication with the processor 36 and includes a display screen. The display screen is an electronic screen (e.g., flat screen LED, LCD, etc.) operable to display the calculated results and/or a digital image of the centrifuged sample. The sample data display 38 has an optical resolution great enough to permit evaluation of the image by a technician. The sample data display 38 may be integral with the housing 30, or may be an independent device in communication with the processor 36. For example, universal monitors are often used in medical facilities, which monitors have the capability of displaying data from more than one analysis device. In such an application, the data to be displayed may be viewed on an integral display screen and/or a remotely located display device in communication with the processor 36.

The present analysis device 28 typically includes an operator input device 40 (e.g., key pad, touch screen, etc.) that allows an operator to enter information relevant to the analysis at hand. For example, the input device 40 can be used to enter information relevant to the analysis such as patient identification and demographics, insurance and billing information, analysis device technical data, test time and location, etc., which information can then be sent along with the sample image signals and/or the analysis results to the remotely located analysis station 29. At the remotely located analysis station 29, trained analysis operators evaluate the information and provide one or more of analysis results, quality control data, etc.

The analysis device 28 includes a communication port 50 for sending and/or receiving information signals relevant to the analysis at hand. For example, the communication port 50 is adapted to send and receive signals representative of one or more of the sample image, analysis results, quality control data, patient identification and/or contact information, etc., between the analysis device 28 and the remotely located analysis station 29 or a remotely located portal 31. The information may be sent in encrypted form for privacy and/or regulatory reasons. The information may be patient specific (e.g., unprocessed image data, test results, billing info, etc.), or analysis device specific (e.g., calibration data, performance data, and/or usage data, etc.), and may be selectively edited (e.g., hospital billing office gets billing data, but not patient analysis data, etc.). The information communicated to the remote analysis station 29 may be unprocessed or partially processed sample image signals. The information processed at the remote station 29 can then be received back at the analysis device 28 via the communications port 50, and/or sent to a remotely located portal 31. Similarly, information processed within the analysis device 28 (e.g., test results) may be sent from the analysis device 28 to one or more remotely located portals 31. The communication port 50 can be a hardwire port for communicating by hardwire connection to the remote analysis station 29, or it can be a wireless communication connection (e.g., similar to that used in a wireless phone).

In some embodiments, fiduciary marks 52 (i.e., calibration, measurement marks; e.g., see FIG. 2) may be placed on or in the capillary tube 10, or the tube holder 32, or on a measuring device positioned adjacent the tube 10 (e.g., a ruler) to facilitate geometric and/or optical calibration and thereby account for any image distortion introduced by the camera. In those instances where the fiduciary marks are placed on or in the tube, a particularly useful embodiment is one wherein the marks are positioned relative to the internal cavity to permit geometric evaluation of sample within the internal cavity. In those instances where fiduciary marks 52 are disposed on a measuring device positioned adjacent the tube 10, the measurement device can measure along an axis that is maintained parallel to the lengthwise axis (e.g., axial direction) of the tube 10. In such embodiments, the measurement device is preferably in close proximity (e.g., in the same focal plane) as the sample tube 10. Alternately, a look-up-table can be provided by factory calibration to serve this function. During the image processing and analysis steps, the calibration information can be used to ensure correct length measurements of the tube features, regardless of their position in the image frame or distance from the camera and can compensate for instrument-to-instrument differences.

The remotely located analysis station 29 includes a processor 54 and a data display 56. The processor 54 is adapted in similar manner to the processor 36 described above; e.g., adapted to process image signals to produce information relating to bands 24 of interest within the image. Similarly, the extent of the information relating to the bands 24 produced by the remotely located processor 54 can be varied to suit the tasks at hand, including the production of analysis data (e.g., CBC, hematocrit, WBC count, etc.) based on the image of the centrifuged sample. The remotely located analysis station 29 may be configured for stationary use (e.g., at an analysis lab where trained operators are located) or may be configured for mobile use (e.g., a portable device that can be readily transported by a physician or technician).

An acceptable remotely located portal 31 is one that is operable to receive information from the analysis device 28 or the remotely located analysis station 29. The remotely located portal has display capability to show information (e.g., text, graphics, etc), and in some embodiments includes the ability to display an image of the centrifuged sample. The display capability can be in the form of an electronic representation on a screen (e.g., real time display on an LED or LCD screen, etc.) or it can be tangible form (e.g., printed document, or electronic file—pdf, tiff, etc.) Like the analysis station 29, the remotely located portal 31 may also be configured for stationary use (e.g., at a doctor's office, insurance carrier office, etc.) or may be configured for mobile use (e.g., a portable device that can be readily transported by a physician, technician, or patient; i.e., the patient's cell phone).

A cell phone type device is a specialized example of a device that can be utilized as either an analysis device 29 or a portal 31. For example, a cell phone having a processor and camera can be adapted using a software package (e.g., programmed using an "APPS") to collect the sample image and perform the analysis on the sample image, thereby acting as an analysis station. The cell phone could also be adapted to send the image and/or the analysis results to a remote portal 31. Alternatively, a cell phone can be adapted to act as a portable portal 31, receiving information from the analysis device 28 or the remotely located analysis station 29.

An example of the manner in which an integral cell phone camera can be used to image a QBC® tube is as follows: The centrifuged QBC® tube may be inserted into a non-disposable, inexpensive QBC® tube holder for imaging by the camera. The tube holder may consist of a box, for example approximately 6 inches deep, 6 inches wide, and 4 inches high, with a provision for attachment of a camera at a viewing orifice and means of securely holding the tube for imaging. The interior surfaces of the box are preferably non-reflective. Illumination may be provided by a number of different sources; e.g., a white and blue LED, or ambient light transmitted through a translucent panel, etc. The QBC® tube is imaged using the cell phone's camera and images are taken with the aforesaid light source. In those embodiments that use multiple different light sources (e.g., blue and white LEDs), it is possible to perform both illuminations at the same time and take one image. A blocking filter and simple magnifier may be present over the camera orifice of the viewing box to prevent reflected blue light from being imaged by the camera and to increase the resolution of the buffy coat. The camera will take the image and can send the image to either a remote analysis station 29 for analysis, and/or the camera can be programmed (e.g., the camera processor can be adapted via a downloaded "APP") to perform the analysis at the point of care and transmit the results as indicated.

Operation:

A fluid sample (e.g., whole blood) is collected from a patient and deposited into a capillary tube 10 such as those used in the QBC® hematology system for subsequent centrifugation. As indicated above, the centrifuge may be independent of, or incorporated into, the analysis device 28. The sample is centrifuged for a period of time adequate to create constituent layer separation within the sample disposed in the tube 10, and the representative bands 24 associated therewith. The centrifuged sample is then imaged using the sample imaging device 34. The image includes substantially all of the radial width 18 and axial length 20 of the sample residing within the internal cavity 16 of the tube 10 in the region where the float 22 resides after centrifugation. Because capillary tubes 10 are not always filled with the exact same volume of fluid sample, the sample imaging device 34 preferably images the region 48 of the tube 10 from the top meniscus to the bottom of the red blood cell layer. It is desirable, but not required, that the bottom of the tube 10 be imaged as well. If the sample being imaged is disposed within a STAR™ type QBC® tube, for example, the total length between the tube bottom to the tube top fill position is approximately 53 mm. The distance from the tube top fill position to the bottom of the float 22 in most instances is about 37 mm. In those device 28 embodiments that include a centrifuge, the sample may be centrifuged and the centrifuge subsequently stopped or slowed to a very low rotational speed prior to the imaging. The sample imaging device 34 produces signals representative of each image and communicates those signals to the processor 36.

The image signals are subsequently analyzed within the processor 36,54 of one or both of the analysis device 28 and the remotely located analysis device 29. The processor(s) 36,54 uses image processing algorithms to isolate and analyze the bands 24 of interest within the sample, and in some instances relevant sections of the bands 24. The analysis produces information (e.g., CBC, hematocrit, WBC count, etc.) based on the physical characteristics of the different bands 24 within the centrifuged sample. The relationship between the physical characteristics of the bands 24 and the desired information (e.g., CBC, hematocrit, WBC count, etc.) is known, for example, from the teachings of U.S. Pat. No. 5,132,087, which is incorporated by reference above.

In a first embodiment of the operation of the present system, unprocessed image signals are sent from the analysis device 28 to the remotely located analysis station 29. In this embodiment, the operator of the analysis device 28 images a centrifuged sample using the analysis device 28, and the "unprocessed" image of the centrifuged sample is sent to the remotely located analysis station 29. The remote analysis station 29 may be operated by a technician sufficiently trained so that he or she may analyze the sample image in a non-CLIA waived setting. The processor 54 within the remote analysis station 29 uses image processing algorithms to analyze the sample bands 24 of interest, and produces information based on the physical characteristics of the different bands 24, as described above. The image of the bands 24 of interest within the centrifuged sample is displayed on the data display of the analysis station 29 to allow the technician to perform a visual analysis of the sample image. In this embodiment of the present system 26, the local analysis device 28 may not have sample image analysis capability or a data display 38. For example, a local analysis device 28 includes a sample imaging device 34 and a communication port 50 adapted to send signals representative of the imaged sample to the remote analysis station 29, and receive information back from the remote analysis station 29.

In a second embodiment of the operation of the present system, image signals produced by the sample imaging device 34 within the local analysis device 28 are at least partially processed within the local analysis device 28, and are subsequently sent to the remotely located analysis station 29 where a trained technician may analyze the processed results and the sample image. The analysis enabled by the remote analysis station 29 and the trained technician can serve a variety of different functions. For example, the display screen 56 of the remote analysis station 29 permits a trained technician to view the actual sample image, including substantially all of the radial width 18 and axial length 20 of the sample residing within the internal cavity 16 of the tube 10 in the region where the float 22 resides after centrifugation. The discerning eye of a trained technician can assess image variables that are not accounted for in even the most comprehensive automated system. Consequently, the ability of the present system 26 to have a trained technician view the sample image is a significant advantage over, for example: a) CLIA waived systems, that do not involve a trained technician; and b) analysis systems that require a trained technician at each location.

The remotely located analysis station 29 can serve a variety of different functions. For example, as indicated in the first operational embodiment described above, the remote analysis station 29 can be the only site for image analysis. In those instances where a CLIA waiver is not available, the present system allows sample images to be collected at local offices and subsequently sent to a remote central office having the analysis station 29 where a trained technician can perform the analyses, and send the results back to the local office or elsewhere if desired.

As another example of function, in situations where a sample may normally be analyzed locally, but a trained technician is not available, untrained personnel can prepare and image the sample and send the image to a central office having an analysis station 29 for faster results. In instances where a trained technician is not available locally, the analysis device 28 may include a lock-out function (e.g., programming) that prevents an unauthorized user from analyzing a sample using the analysis device 28.

As another example of function, in those instances where local analysis devices 28 perform the analyses on the sample images, the respective sample image can be sent to the remote analysis station 28 where the sample image can be independently analyzed using the analysis station 29 for quality control purposes. The processor 36 of the local analysis device 28 can be programmed, for example, to automatically send a representative sample image to the remote analysis station 29 on a time basis (i.e., periodic), a use basis (i.e., a number of analyses performed), or randomly for quality control purposes. Alternatively, the local sample images can automatically be sent to the remote analysis station 29 for confirmation of result. The trained technician operating the remote analysis station 29 can evaluate the sample image for potential problems; e.g., overall image quality, accuracy of sample coloration, the degree to which a blood sample may be lipemic or icteric, whether the assigned band boundary markings are accurately positioned relative to the sample image, etc. If the remotely located technician determines the local analysis device 28 is not operating correctly, that technician can prevent data release or otherwise shut down the local analysis device 28 via the remotely located analysis station 29.

A person of skill in the art will recognize that automated analysis systems very likely cannot account for every possible problem that may be encountered during a sample image analysis. The present system addresses this issue through the use of the remote located analysis station 29. For example, sometimes during centrifugation sample will spill out of the capillary tube 10 and pass into the retaining tube of the centrifuge. In such instances, the released sample can contaminate the exterior of the capillary tube 10 and inhibit accurate image analysis. Because the specific contamination is random and will likely vary considerably from incident to incident, it would be very difficult for an automated local analysis device 28 to correctly identify all types of external contamination. Similarly, a misplaced tube label or debris deposited on the exterior of the capillary tube 10 during handling can also inhibit or prevent accurate image analysis. In these instances, the present system 26 allows the sample image produced on an automated analysis device 28 (which sample may be flagged as having an unidentifiable issue) to be remotely analyzed by a trained technician at an analysis station 29, which technician can then account for such image anomalies or determine that the sample image cannot be used.

In addition to the analysis system 26 operating functions described above, the present system also allows for the comparison of current sample image analysis data to be compared against previous results, or standards, and appropriate warnings or flags can be sent to the health care provider if current results differ significantly from previous ones, or if a limit is exceeded. Additional operational benefits could arise if the returning reports contain hypertext links to the patient's contact information so the patient's email address and/or phone can be automatically accessed by the care provider by simply activating the link, thus avoiding the necessity for looking up the information up.

The present system 26 can also be implemented as a business model wherein an analysis provider provides relatively low cost analysis devices 28 to medical offices, which devices 28 are in communication with a central analysis station 29 which is operated by the provider's trained technicians. The local medical office can acquire the sample, and prepare a sample image using the local analysis device 28. The sample image is subsequently communicated to the central office of the service provider, where a trained technician performs an analysis on the sample image using an analysis station 29. The results of the test can subsequently be sent from the centrally located analysis station 29 back to the local medical office, or to a remote portal 31 (e.g., the physician's portal 31 or the patients's cell phone, etc.).

Although the invention has been described and illustrated with respect to exemplary embodiments thereof, the foregoing and various other additions and omissions may be made therein and thereto without departing from the spirit and scope of the present invention.

What is claimed is:

1. A system for analyzing a hematologic sample centrifuged within a capillary tube, which tube has an internal compartment with a radial width and an axial length and a float disposed within the tube, the device comprising:
   at least one first analysis device that includes a tube holder, a sample imaging device adapted to capture a single digital image of the sample residing within a region of the tube, which single image depicts substantially all of the radial width and axial length of the sample residing within the internal cavity of the tube where the float resides after centrifugation, which image is created while the sample image device and the tube are positionally static relative to one another for a period of time adequate to create the single image, and the sample imaging device is adapted to produce signals representative of the image; and
   a second analysis device adapted to be remotely located from the first analysis device, and adapted to communicate with the first analysis device, including receiving the signals representative of the image, which second analysis device includes a processor adapted to produce information relating to bands of interest within the image based on the signals, and a sample data display adapted to display the digital image of the sample within the region.

2. The system of claim 1, wherein the first analysis device includes a processor adapted to produce information relating to bands of interest within the image based on the signals from the sample imaging device.

3. The system of claim 2, wherein the processor of the first analysis device is adapted to selectively lock out unauthorized operators.

4. The system of claim 2, wherein processor of the first analysis device is adapted to transmit the signals representative of the image to the second analysis device in the event an anomaly within the image is detected by the processor of the first analysis device.

5. The system of claim 1, wherein the second analysis device is adapted to send the information relating to bands of interest within the image to one or both of the first analysis device and a remote portal.

6. The system of claim 1, wherein the sample imaging device is a digital camera.

7. The system of claim 6, wherein the digital camera is operable to create a single image of the region of the tube, wherein the region is defined by substantially all of the width and axial length of the sample within the tube.

8. The system of claim 1, wherein the first analysis device is adapted to send the signals representative of the image to the second analysis device on a periodic basis.

9. The system of claim 1, wherein the first analysis device is adapted to send the signals representative of the image to the second analysis device on a use basis.

10. A method for performing an analysis of hematologic samples deposited within a capillary tube, which tube has an internal cavity with a radial width and an axial length, and a float disposed within the tube, the method comprising the steps of:
    creating a single image of a region of a sample centrifuged within a capillary tube using a first analysis device, which single image depicts substantially all of the radial width and axial length of the sample residing within the internal cavity of the tube where the float resides after centrifugation, and which first analysis device includes a sample imaging device, and which single image is created with the sample image device and the tube positionally static relative to one another for a period of time adequate to create the single image;
    communicating the signals representative of the image to a second analysis device independent of, and remotely located from, the first analysis device;
    processing the signals representative of the image using the second analysis device and producing analysis data based on the signals; and
    displaying the image of the region of the sample using the second analysis device.

11. The method of claim 10, further comprising the step of communicating the analysis data to the first analysis device.

12. The method of claim 10, further comprising the step of evaluating the analysis data for quality control and producing quality control data.

13. The method of claim 12, further comprising the step of communicating the quality control data to the first analysis device.

14. The method of claim 10, further comprising the step of processing the signals representative of the image using the first analysis device and producing analysis data based on the signals, and communicating the analysis data to the second analysis device.

15. The method of claim 14, further comprising the step of requiring an operator authorization prior to releasing or reporting results based upon the signals representative of the image using the first analysis device.

16. The method of claim 14, further comprising the step of evaluating the signals representative of the image using the first analysis device for an anomaly within the image and communicating the presence of the anomaly to the second analysis device in the event an anomaly within the image is detected.

17. The method of claim 14, further comprising the step of periodically sending the signals representative of the image to the second analysis device.

18. The method of claim 14, further comprising the step of sending the signals representative of the image to the second analysis device on a use basis.

19. The method of claim 10, wherein the step of imaging the region of sample includes imaging substantially all of the width and axial length of the sample within the tube.

20. The method of claim 10 further comprising the step of communicating data relating to the analysis to a portal located remotely from the first and second analysis devices.

* * * * *